(12) United States Patent
Pinto Gómez

(10) Patent No.: US 12,181,430 B2
(45) Date of Patent: Dec. 31, 2024

(54) SYSTEM AND METHOD FOR THE DETECTION AND DIGITALIZATION OF THE STATE OF FRESH CONCRETE USING INFRARED THERMOGRAPHY AND MATHEMATICAL TREND FUNCTIONS

(71) Applicant: SOLUCIONES DE INNOVACIÓN DIGITAL SPA, Santiago (CL)

(72) Inventor: Emiliano Andrés Pinto Gómez, Santiago (CL)

(73) Assignee: SOLUCIONES DE INNOVACIÓN DIGITAL SPA, Santiago (CL)

( * ) Notice: Subject to any disclaimer, the term of this patent is extended or adjusted under 35 U.S.C. 154(b) by 793 days.

(21) Appl. No.: 17/271,085

(22) PCT Filed: Aug. 8, 2019

(86) PCT No.: PCT/CL2019/050069
§ 371 (c)(1),
(2) Date: Feb. 24, 2021

(87) PCT Pub. No.: WO2020/041912
PCT Pub. Date: Mar. 5, 2020

(65) Prior Publication Data
US 2021/0318258 A1    Oct. 14, 2021

(30) Foreign Application Priority Data

Aug. 30, 2018 (CL) .................................. 2477-2018

(51) Int. Cl.
*G01N 25/48* (2006.01)
*G01J 5/48* (2022.01)
(Continued)

(52) U.S. Cl.
CPC ....... *G01N 25/4846* (2013.01); *G06T 7/0004* (2013.01); *G01J 2005/0077* (2013.01);
(Continued)

(58) Field of Classification Search
CPC .............. G01N 25/4846; G06T 7/0004; G06T 2207/10048; G06T 2207/20024; G06T 2207/30132; G01J 5/485; G01J 2005/0077
See application file for complete search history.

(56) References Cited

U.S. PATENT DOCUMENTS

| 2010/0088041 A1* | 4/2010 | Ringermacher ....... G01N 25/72 |
| | | 702/40 |
| 2012/0119088 A1* | 5/2012 | Honda .............. H01L 27/14649 |
| | | 250/332 |

(Continued)

FOREIGN PATENT DOCUMENTS

| JP | 2012221235 A | 11/2012 |
| WO | 2015001344 A1 | 1/2015 |

OTHER PUBLICATIONS

Dataraker DT515, 2015.*
(Continued)

*Primary Examiner* — Mohamed Charioui
*Assistant Examiner* — Lynda Dinh
(74) *Attorney, Agent, or Firm* — Procopio, Cory, Hargreaves & Savitch LLP

(57) ABSTRACT

A system and a computer-implemented method, for detecting concrete using infrared thermography, allow to detect concrete in a region containing zones in which concrete exists and zones in which concrete does not exist. The system for detecting the concrete includes an infrared camera for obtaining a plurality of infrared thermography images in a time range from a region containing fresh concrete, an ambient temperature sensor for obtaining ambient temperature measurements, and a processor connected to the camera and to the ambient temperature sensor.

14 Claims, 5 Drawing Sheets

(51) Int. Cl.
*G06T 7/00* (2017.01)
*G01J 5/00* (2022.01)
(52) U.S. Cl.
CPC ..... *G01J 5/485* (2022.01); *G06T 2207/10048* (2013.01); *G06T 2207/20024* (2013.01); *G06T 2207/30132* (2013.01)

(56) References Cited

U.S. PATENT DOCUMENTS

2015/0254860 A1\* 9/2015 Wang .................... G06F 18/285
 382/190
2018/0372487 A1\* 12/2018 Irie ........................ G01N 25/18

OTHER PUBLICATIONS

International Search Report and Written Opinion for related PCT App No. PCT/CL2019/050069 dated Feb. 10, 2020, 13 pgs.
Azenha, M., et al., Thermography as a Technique for Monitoring Early Age Temperatures of Hardening Concrete, Construction and Building Materials, 25, 2011, pp. 4232-4240.

\* cited by examiner

SYSTEM AND METHOD FOR THE DETECTION AND DIGITALIZATION OF THE STATE OF FRESH CONCRETE USING INFRARED THERMOGRAPHY AND MATHEMATICAL TREND FUNCTIONS

CROSS-REFERENCE TO RELATED APPLICATIONS

This application is a U.S. National Stage entry of PCT Application No: PCT/CL2019/050069 filed Aug. 8, 2019, which claims priority to Chilean Patent Application No. 2477-2018 filed Aug. 30, 2018, the contents of which are incorporated herein by reference.

TECHNICAL FIELD OF THE INVENTION

The present invention is related to the field of measuring or testing, particularly to the use of thermal means for analyzing materials and specifically provides a system and a method for detecting concrete by means of infrared thermography.

BACKGROUND OF THE INVENTION

In the building sector, a recurrent problem is monitoring the progress of the construction work, as well as the curing time of the concrete. However, for monitoring the progress of the construction work it is required, in first place, to detect the concrete on site, in order to provide a further digitalization In the prior art, it is known that the curing of the concrete is an exothermic reaction. Once the concrete has been poured into a formwork, the cement paste starts an internal curing process which releases heat inside the mixture, producing a rise in the temperature. The previous has made infrared thermography for studying structures containing concrete to be widely disclosed in the prior art.

For example, some documents of the prior art provide solutions related to the detection of flawed portions in slabs or walls. In this sense, the patent document JP 5017507 describes a method for detecting flawed portions in civil works, for example, made of concrete. To achieve this, the temperature gradient along a direction of interest is examined in a thermographic image. Said temperature gradient is obtained by means of the comparison of the temperature in a pixel with the average temperature of some of its adjacent pixels. Subsequently, a value (e.g. right/defective) is assigned to said pixel. In this way, additionally, it allows to obtain a geometry of the flawed portion.

The document WO 2015/001344, on its hand, describes a method for determining the strength of a shotcrete structure inside a tunnel by means of thermographic images. To achieve this, the method obtains a plurality of thermographic images and, from them, a plurality of temperature profiles as a function of the time for each pixel. In order to obtain a strength degree of a portion, said temperature profiles as a function of the time are compared to standard curves.

On the other hand, Azenha, et al. (Miguel Azenha, Rui Faria y Helena Figueiras, *Thermography as a technique for monitoring early age temperatures of hardening* concrete, Construction and Building Materials 25 (2011) 4232-4240) describe the use of thermographic images for monitoring concrete in early curing stages. Particularly, they study the evolution of the surface temperature over time and compare said measurements to computer simulations in order to predict the future behavior of said samples.

Nevertheless, the solutions of the prior are defective in order to detect concrete in a region containing zones in which concrete exists and zones in which concrete does not exist. For example, according to the method described in JP 5017507, all the boundary between a zone containing concrete and a zone not containing concrete would be detected as a flaw.

On the other hand, in the method described in WO 2015/001344, all the captured image corresponds to concrete, therefore a detection of the same lacks sense. This is particularly relevant in a civil work, in which, additionally to the teams making common jobs, there are materials other than concrete, such as steel, formworks (panels for slabs and vertical props or dropheads), metallic structures, among others that must be differentiated from concrete.

Consequently, a system and a method for detecting concrete by means of infrared thermography is required for overcoming the deficiencies of the prior art.

SUMMARY OF THE INVENTION

The present invention provides a system for detecting concrete by means of infrared thermography that is characterized in that it comprises: an information storage memory; and a processor operatively connected to said memory and configured to read information from said memory and to store information in said memory; wherein said processor is configured to: store a plurality of infrared thermography images in said memory, wherein each image of said plurality corresponds to a region containing fresh concrete and wherein said plurality of images corresponds to a time range; obtain for each pixel of said plurality of images, a temperature profile as a function of time; obtain a plurality of curves of temperature as a function of time, each of said temperature curves fitting a corresponding temperature profile as a function of the time; determine an indicating value from each of said curves of temperature as function of time; and define that a pixel corresponds to concrete when said indicating value is greater that a threshold value.

In a preferred embodiment, the system is characterized in that it additionally comprises an ambient temperature sensor operatively connected to said processor sensor and in that said processor is additionally configured to: obtain ambient temperature measurements form said ambient temperature sensor; and store information corresponding to the ambient temperature in said memory.

In another preferred embodiment, the system is characterized in that it additionally comprises an infrared camera operatively connected to said processor and in that said processor is additionally configured to: control said infrared camera; obtain infrared thermography images from said infrared camera; and store said infrared thermography images in said memory.

In other object of the present invention, it is provided a method for detecting concrete by means of infrared thermography that is characterized in that it comprises the steps of: storing a plurality of infrared thermography images in an information storage memory, wherein each image of said plurality corresponds to a region containing fresh concrete and wherein said plurality of images corresponds to a time range; obtaining, for each pixel of said plurality of images, a temperature profile as a function of the time by means of a processor operatively connected to said information storage memory; obtaining a plurality of curves of temperature as a function of time, each of said temperature curves fitting a corresponding temperature profile as a function of the time by means of said processor; determining an indicating value from said curves of temperature as a function of time by means of said processor; and define that a pixel corresponds to concrete when said indicating value corresponding to said pixel is greater than a threshold value by means of said processor.

In a preferred embodiment, the method is characterized in that said curve of temperature as a function of time is selected from the group formed by: low coefficient Fourier series or low coefficient polynomials.

In another preferred embodiment, the method is characterized in that it additionally comprises: storing information corresponding to an ambient temperature profile in said memory; obtaining a curve of ambient temperature as a function of time by means of said processor; and obtaining said threshold value from said curve of ambient temperature as a function of time by means of said processor. In a further preferred embodiment, the method is characterized in that said indicating value is the difference between the maximum temperature and the initial temperature in said time range and in that said threshold value is the difference between the maximum ambient temperature and the minimum ambient temperature in said time range. In another further preferred embodiment, the method is characterized in that said indicating value is the area under the curve in said time range and in that said threshold value is selected from the group formed by the area under the curve of ambient temperature in said time range; and the product of the average ambient temperature value in said time range and the length of said time range.

In an additional preferred embodiment, the method is characterized in that said time range is between 3 hours and 12 hours.

In another preferred embodiment, the method is characterized in that each image of said plurality of infrared thermography images is obtained with a periodicity between 5 minutes and 30 minutes.

In a preferred embodiment, the method is characterized in that each image of said plurality of images is filtered before the obtention of said temperature profiles as a function of time. In a further preferred embodiment, the method is characterized in that said plurality of images is filtered by means of a gaussian filter.

In another preferred embodiment, the method is characterized in that it additionally comprises generating an image of said region containing fresh concrete wherein the pixels identified as concrete are colored in a first color, said first color being contrasting to said image, said image being generated by means of said processor.

In an additional preferred embodiment, the method is characterized in that it additionally comprises generating a binary map of said region containing fresh concrete by means of said processor.

DETAILED DESCRIPTION OF THE INVENTION

Figure 1:
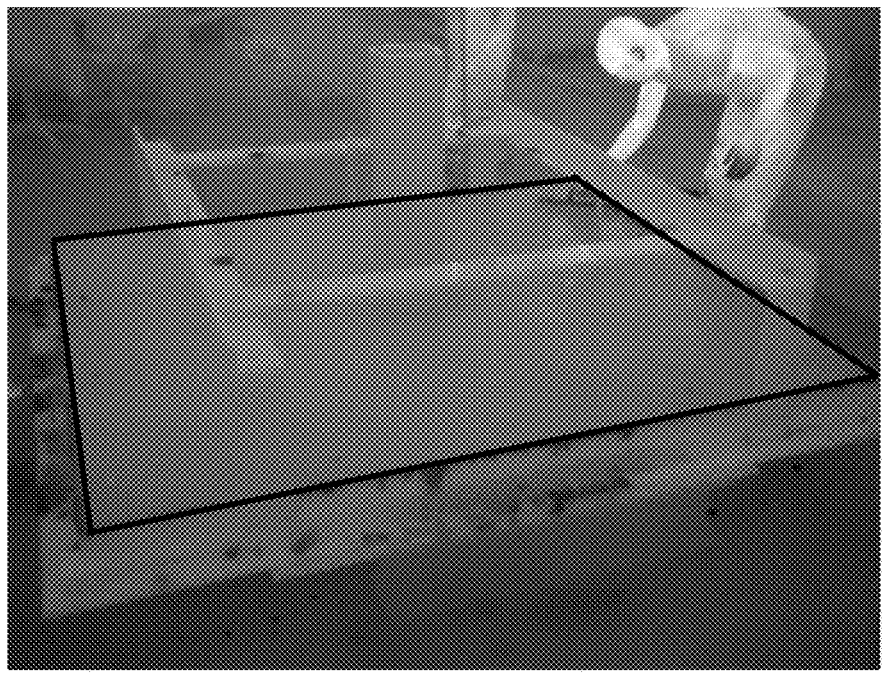
FIG. 1 shows a thermographic image of a region having a portion containing concrete and a portion not containing concrete.

Following, the present invention will be described in detail, referring to the figures accompanying the present application.

Essentially, the invention provides a system for detecting concrete by means of infrared thermography, essentially comprising:
   an information storage memory; and
   a processor operatively connected to said memory and configured to read information from said memory and to store information in said memory;
wherein said processor is configured to:
   store a plurality of infrared thermography images in said memory, wherein each image of said plurality corresponds to a region containing fresh concrete and wherein said plurality of images corresponds to a time range;
   obtain, for each pixel of said plurality of images, a temperature profile as a function of time;
   obtain a plurality of curves of temperature as a function of time, each of said temperature curves fitting a corresponding temperature profile as a function of time;
   determine an indicating value from each of said curves of temperatures as a function of time; and
   define that a pixel corresponds to concrete when said indicating value corresponding to said pixel is greater than a threshold value.

Additionally, the present invention provides a method for detecting concrete by means of infrared thermography that is characterized in that it comprises the steps of:
   storing a plurality of infrared thermography images in an information storage memory, wherein each image of said plurality corresponds to a region containing fresh concrete and wherein said plurality of images corresponds to a time range;
   obtaining, for each pixel of said plurality of images, a temperature profile as a function of time by means of a processor operatively connected to said information storage memory;
   obtaining a plurality of curves of temperature as a function of time, each of said temperature curves fitting a corresponding temperature profile as a function of time by means of said processor;
   determining an indicating value from each of said curves of temperature as a function of time by means of said processor; and
   defining that a pixel corresponds to concrete when said indicating value corresponding to said pixel is greater than a threshold value by means of said processor.

In the context of the present invention, it must be understood that an infrared thermography image corresponds to a digital image obtained in the infrared spectrum, in such a way that the intensity being measured in each pixel is correlated to the surface temperature in that point. In some preferred embodiment, without limiting the scope of the present invention, said infrared thermography image is modified in order to make it visible to the human eye, in such a way that the color of a pixel in said image is an indicator of the temperature being measured in said point. Along this specification, the terms infrared thermography image and thermographic image will be indistinctly used for referring to an infrared thermography image.

The way in which said plurality of infrared thermography images is stored in said information storage memory does not limit the scope of the present invention. For example, and without limiting the scope of the present invention, said memory may be a non-volatile memory and said plurality of infrared thermography images may be stored in said storage memory directly from the camera with which said plurality of infrared thermography images are captured. However, in other preferred embodiment, said infrared thermography image capturing camera may be operatively connected to said processor, in such a way that is said processor who stores said images in said memory. In this last case, said memory may be both, a volatile or non-volatile memory without limiting the scope of the present invention.

Either said memory is volatile or non-volatile, the specific nature of said information storage memory does not limit the scope of the present invention. On the other hand, the storage capacity of said memory does not limit the scope of the present invention, as long as it is enough for storing said plurality of infrared thermography images.

On the other hand, said processor is operatively connected to said memory and is configured to read information from said memory and write information in said memory. Additionally, said processor is configured to perform operations from the information being stored in said memory. In a preferred embodiment, without limiting the scope of the present invention, said processor may obtain said configuration to execute the steps being part of the method of the present invention from a factory setting. In this last case, it will be referred as a dedicated processor.

However, in other preferred embodiments, without limiting the scope of the present invention, said processor may obtain said configuration to execute the steps being part of the method of the present invention by means of the execution of a suitably written computer program for such effect. In this last case, the nature of said computer program, the support in which it is written, as well as the programming language used for its writing do not limit the scope of the present invention, and any option known to a person ordinarily skilled in the art may be used.

According to the first step of the method of the present invention, a plurality of infrared thermography images is stored in an information storage memory. Each image of said plurality corresponds to a region containing fresh concrete. It must be understood that a region containing fresh concrete has portions containing concrete and may have portions not containing concrete. For example, and without limiting the scope of the present invention, in FIG. 1 it is shown a thermographic image in which the portion containing concrete has been enclosed in a black polygon, whereas all the region around said polygon is a region without concrete.

On the other hand, said infrared thermography images are captured without a movement or displacement of the camera capturing said images existing. In this way, the fixed structures do not show a relative movement between consecutive images. The previous allows a same position (m,n) in different images to substantially correspond to the same point, in which m corresponds to the row of a pixel and n to the column of said pixel in an image.

Nevertheless, occasionally, a mobile structure or object may interfere in one of the thermographic images of said plurality. One of the advantages of the system and method of the present invention, and that will be explained in detail later, is that they allow to detect the portion containing concrete even in these cases.

In any of the preferred embodiments, for a particular infrared thermography image, it is possible to obtain a matrix of temperatures corresponding to said image. For effects of the present detailed description, and without limiting the scope of the present invention, said temperature matrix will be expressed as $T(m,n)$, in which m is the row of a pixel of interest in the infrared thermography image and n is the column of said pixel in said image.

Said temperature matrix may be obtained, without limiting the scope of the present invention, directly from the camera from which the infrared thermography image was obtained or may be obtained after the acquisition of said plurality of images. In said second case, said temperature matrix is obtained by means of a mathematical treatment of the obtained image, that is performed by said processor. Said temperature matrix may be obtained by means of any method known in the prior art without limiting the scope of the present invention. Given a kind of thermographic image, a person ordinarily skilled in the art may be determine the mathematical treatment needed to obtain said temperature matrix.

For example and without limiting the scope of the present invention, if said thermographic image is an image that has been modified to be perceptible by the human eye by including a colored temperature scale, said processor may make a correspondence between the color of a pixel of interest and the corresponding temperature to that color. In other preferred embodiments, without limiting the scope of the present invention, said thermographic image may be an image in which the colored scale corresponds to the intensity of infrared radiation being captured in the corresponding pixel. In this last case, the processor, in addition of making a correspondence between the color of a pixel and the corresponding intensity, performs a mathematical treatment that allows to correlate said intensity to the corresponding temperature to that pixel.

On the other hand, said plurality of thermographic images correspond to a time range. Said time range may be any range that allows to detect concrete in said plurality of thermographic images. For example, and without limiting the scope of the present invention, FIGS. 2 to 7 show binary images obtained by means of a preferred embodiment of the system and method of the present invention, in which said time range is between 0.58 hours and 6.83 hours. However, the time range may be, for example and without limiting the scope of the present invention, between 3 hours and 12 hours.

In this way, the processor is configured to obtain a plurality of temperatures $T(m,n,t)$, wherein t is the time in which the corresponding image has been captured. Said time t may be obtained, for example and without limiting the scope of the present invention, from the metadata of the obtained thermographic image. In this last case, without limiting the scope of the present invention, said processor is configured to obtain said time t from said metadata.

In other preferred embodiment, without limiting the scope of the present invention, said plurality of thermographic images may be obtained at regular time intervals, in such a way that the image number is correlated to the time in which the same was captured. In this last case, the processor is configured to determine the image number, as well as to assign a time t to said image. The periodicity with which said plurality of thermographic images is captured does not limit the scope of the present invention. Said plurality of images may be captured, for example and without limiting the scope of the present invention, with a periodicity between 1 minute and 120 minutes, more preferably between 2 minutes and 60 minutes and even more preferably between 5 minutes and 30 minutes.

According to the previously described, for each position of a pixel (m,n), it is possible to obtain a set of temperature values as a function of time, T(m,n,t), which must be understood as a temperature profile as a function of time for that pixel. Said processor is configured to obtain said temperature profile from the plurality of images being stored in the memory.

Additionally, in a preferred embodiment and without limiting the scope of the present invention, the processor may be configured to filter each thermographic image being part of the plurality of thermographic images before obtaining said temperature profiles. Said filtering process has the objective of eliminating the noise from said plurality of thermographic images. The method by means of which said plurality of thermographic images is filtered does not limit the scope of the present invention and may be, without limiting to those, a gaussian filter, a low-pass filter, an average filter or a median filter.

In a further preferred embodiment, said processor is configured to filter said plurality of thermographic images by means of a gaussian filter. The parameters that define said gaussian filter, particularly the variance, do not limit the scope of the present invention. In another further preferred embodiment, said processor is configured to filter said plurality of thermographic images by means of a low-pass filter. In this case, the cut-off frequency of said low-pass filter does not limit the scope of the present invention.

In both cases, the case in that said plurality of thermographic images are filtered and the case in that said plurality of images are not filtered, said temperature profile as a function of time makes it possible to determine whether the pixel in question corresponds to concrete. Nevertheless, in contrast to the prior art, in which said temperature profile as a function of time is compared to an standard curve, in the case of the method of the present invention said processor is configured to fit said temperature profile as a function of time by means of a curve of temperature as a function of time. In this way, for each position of a pixel, (m,n), said processor obtains a curve of temperature as a function of time, defining a plurality of curves of temperature as a function of time.

In the context of the present invention, it must be understood that a curve of temperature as a function of time is a mathematical function capable of being evaluated at any time between the initial and final time of capture of the thermographic images. In contrast, a temperature profile as a function of time corresponds to a discrete set of temperature points.

Additionally, said fitting by means of a curve of temperature as a function of time must consider that, occasionally, there will exist points in the temperature profile as a function of time that do not correspond to the surface to be analyzed. For example, and without limiting the scope of the present invention, in FIG. 1 it is shown, at the upper right corner, the shade of a human figure. However, said person will not be in that position at other times different from the captured in that thermographic image. Additionally, said person will generate an extreme temperature in the temperature profile that could generate false positives.

To reduce or eliminate said false positives, said processor is configured to fit said temperature profile as a function of time by means of a curve of temperature as a function of time that will be called as low coefficient. In this sense, for example and without limiting the scope of the present invention, if the processor is configured to fit said temperature profile as a function of time by means of a polynomial function, the degree of the polynomial will be lower than a certain threshold degree, for example and without limiting the scope of the present invention, of a degree lower than 5. However, in other preferred embodiment, a polynomial having a degree lower than 4 or lower than 3 may be used without limiting the scope of the present invention. In another preferred embodiment, without limiting the scope of the present invention, said processor may be configured to fit said temperature profile as a function of time by means of a curve of temperature that is a gaussian curve. In this last preferred embodiment, said processor is configured to find a central value and a width of said gaussian curve.

In other preferred embodiments, without limiting the scope of the present invention, the processor may be configured to fit said temperature profile as a function of time by means of a curve of temperature as a function of time that is a low coefficient Fourier series. In this sense, a person ordinarily skilled in the art knows that any function f(t) in a finite interval [0,S] may be fitted by means of a Fourier series according to the following equation:

$$f(t) = a_0 + \sum_{l=1}^{\infty}\left(a_l \cos\frac{2l\pi t}{S} + b_l sen\frac{2l\pi t}{S}\right),$$

wherein the way in which said values $\kappa_l$ and $b_l$ are calculated is known to a person ordinarily skilled in the relevant art. In this way, said processor may be configured to obtain said values $a_l$ and $b_l$.

It is to be understood that a low coefficient Fourier series is a Fourier series being truncated at an specific value of l, for example and without limiting the scope of the present invention, at a value of l lower than 5, further preferably lower than 4, and even further preferably lower than 2.

The fittings by means of a low coefficient curve of temperature have the advantage that they eliminate the high frequency components of the curve of temperature as a function of time, therefore any extreme temperature will be softened in said curve, eliminating in this way the occurrence of false positives.

Any curve of temperature that allows to fit the temperature profile as a function of time may be used to implement the method of the present invention without limiting the scope of the same.

From said curves of temperature as a function of time, the processor is configured to determine an indicating value. Said indicating value allows to differentiate a pixel corresponding to concrete from a pixel not corresponding to concrete. For example, and without limiting the scope of the present invention, said indicating value may be an area under said curve of temperature as a function of time. In another preferred embodiment, without limiting the scope of the present invention, said indicating value may be the difference of temperature between the maximum value of said curve of temperature and the initial value of said curve of temperature.

Nevertheless, in other preferred embodiments, it is possible to use other indicating values obtained from the curves of temperature as a function of time without limiting the scope of the present invention. For example, and without limiting the scope of the present invention, it is possible to obtain other indicating values from the maximum temperature and the initial temperature of the curve of temperature, such as the ratio between them, the average between them, of any other weighing between said values.

Said processor is additionally configured to determine whether a pixel corresponds to concrete by means of the comparison between said indicating value and a threshold value. If said indicating value is higher than said threshold value, said processor will determine that said pixel corresponds to concrete. Consequently, if said indicating value is lower or equal than said threshold value, said processor will determine that said pixel does not correspond to concrete.

Said threshold value may be any value that allows to differentiate a pixel corresponding to concrete from a pixel not corresponding to concrete. For example, and without limiting the scope of the present invention, when said indicating value corresponds to the difference between the maximum value of the curve of temperature and the initial value of said curve, said threshold value may be the difference between the maximum and minimum ambient temperature values in said time range. In a preferred embodiment, without limiting the scope of the present invention, the processor is configured to obtain said difference between the maximum and the minimum ambient temperature values in said time range. In a further preferred embodiment, without limiting the scope of the present invention, said threshold value is the difference between the maximum and minimum ambient temperature values plus a tolerance temperature value. Said tolerance temperature value allows to avoid false positives when the variation in the ambient temperature in said time range is too low, for example and without limiting the scope of the present invention, in controlled environment conditions or when the difference of the ambient temperature is lower than 2° C. The magnitude of said tolerance temperature value does not limit the scope of the present invention and may be, without limiting the scope of the present invention, between 0.1° C. and 5° C.

In another preferred embodiment, when said indicating value corresponds to the area under the curve in said time range, said threshold value may be an average ambient temperature value times the length of said time range. In this case, the processor is configured to obtain said average ambient temperature value and to obtain said threshold value from said average ambient temperature value.

In another preferred embodiment the memory additionally stores information corresponding to an ambient temperature profile as a function of time and the processor is additionally configured to obtain a curve of ambient temperature as a function of time and to obtain said threshold value from said curve of ambient temperature as a function of time.

The way in that said information corresponding to an ambient temperature profile is stored in said memory does not limit the scope of the present invention. For example, and without limiting the scope of the present invention, said processor may be operatively connected to an ambient temperature sensor and may be configured to store said information in said memory. In other preferred embodiment, without limiting the scope of the present invention, said plurality of thermographic images may include, a part of the metadata, information related to the ambient temperature, for example, as obtained by means of a sensor being present in the camera that captures said thermographic images. In an additional preferred embodiment, without limiting the scope of the present invention, said information corresponding to an ambient temperature profile may be obtained from an external source, for example and without limiting the scope of the present invention, from the internet. For this, the processor is additionally operatively connected to said external source, for example the internet, and is configured to obtain said information from said external source and to store said information in said memory.

In a preferred embodiment, without limiting the scope of the present invention, when said indicating value corresponds to the difference between the maximum and initial values in said time range, said threshold value may be the difference between the maximum and the minimum temperatures in said curve of ambient temperature. In another example, without limiting the scope of the present invention, when said indicating value corresponds to the area under the curve in said time range, said threshold value may be the area under the curve in said time range in said curve of ambient temperature.

However, in other preferred embodiments and without limiting the scope of the present invention, it is possible to use other threshold values, such as the ratio between the maximum and the minimum ambient temperatures, the ambient temperature average, among others.

According to the system and method previously described, it is possible to detect concrete by means of infrared thermography, specifically from a plurality of infrared thermography images, wherein said plurality of thermographic images corresponds to a region containing concrete and may have portions not corresponding to concrete.

However, in a preferred embodiment and without limiting the scope of the present invention, said processor may be configured to generate images in which the portion corresponding to concrete are explicitly identified. In a preferred embodiment, without limiting the scope of the present invention, said processor is configured to modify one of the thermographic image, for example and without limiting the scope of the present invention, the last thermographic image being stored in the memory, by coloring said pixels corresponding to concrete of a first color being contrasting with said thermographic image.

In another preferred embodiment, said processor is configured to generate a binary map of said region containing fresh concrete. In the context of the present invention it must be understood that a binary map is a matrix of the same size of the thermographic images, wherein the position of a pixel corresponding to concrete stores a first value, for example 1, whereas the position of a pixel not corresponding to concrete stores a second value, for example 0. For example, and without limiting the scope of the present invention, FIGS. 2 to 7 are graphic representation of binary maps obtained by means of an embodiment of the system and method of the present invention at different time ranges.

In an additional preferred embodiment, without limiting the scope of the present invention, said processor is configured to store the values (m,n), respectively corresponding to row and column, of a pixel containing concrete. This preferred embodiment has the advantage of allowing to perform a post processing of the information, for example and without limiting the scope of the present invention, to display said information in an external application or program.

Additionally, the method of the present invention may be implemented in real time or later than the capture of the thermographic images. In a preferred embodiment, without limiting the scope of the present invention, the processor is operatively connected to the camera capturing said thermographic images and is configured to control said camera. In this preferred embodiment, said processor may be configured to obtain said plurality of thermographic images from said camera, to store said plurality of thermographic images in the memory and to perform the operations being part of the method of the present invention. It will be evident to a person ordinarily skilled in the art that, in this case, the method of the present invention may be implemented in real time.

On the other hand, in the cases in which the method and system of the present invention are used in a construction work, it is possible to digitalize the place of the works, in order to allow its incorporation into a building information model (BIM). In this way, additionally and without limiting the scope of the present invention, it is possible to monitor the progress of the works in real time. This can be accomplished, for example and without limiting the scope of the present invention, by means of the determination of indicating parameters of the progress of the works, for example, number of daily, weekly and monthly concreting. Additionally, said indicating parameters of the progress of the works may allow, without limiting the scope of the present invention, to predict the necessity of materials in the future, optimizing in this way the request of quotations and the emission of purchase orders for the acquisition of material.

According to the previously detailed description, it is possible to obtain a system and method for detecting concrete by means of infrared thermography. It must be understood that different preferred embodiments previously detailed may be combined with each other in any way, without limiting the scope of the present invention.

Following, examples of embodiments of the present invention will be exposed. It must be understood that said examples pursue to provide a better understanding of the invention, but in any case, limit the scope of the present invention.

Additionally, aspects being described in different examples may be combined with each other or with other preferred embodiments previously detailed in any way without limiting the scope of the present invention.

Example 1: Acquisition of a Plurality of Infrared Thermography Images

In FIG. 1 it is shown an infrared thermography image captured in a test of the method of the present invention. In this case, a fresh concrete sample was provided. The portion containing fresh concrete has been delimited by means of a black polygon that is not part of the original image, but that was incorporated for a better understanding of the present invention. Additionally, over the fresh concrete portion it is seen a metallic structure surrounding the concrete sample, as well as a general background of the test.

A plurality of infrared thermography images of said concrete sample was obtained at regular intervals of 15 minutes.

Example 2: Obtention of the Temperature Profile and Curve of Temperature as Function of Time FIGS. 8 and 9 show plots of temperature as a function of time corresponding, respectively, to a pixel containing concrete and to a pixel not containing concrete.

In said plots, the label 'A' corresponds to the temperature points measured from the thermographic images, 'B' corresponds to the curve of temperature as a function of time fitting said temperature profile, 'C' corresponds to the variation of ambient temperature and 'D' corresponds to the variation of the ambient temperature in the time range of interest.

Additionally, the values $\Delta T_A$ and $\Delta T_{CD}$, respectively corresponding to the maximum ambient temperature difference and to the difference between the maximum and initial temperatures in the curve of temperature as a function of time in the time range of interest are shown at both figures.

Figure 8:
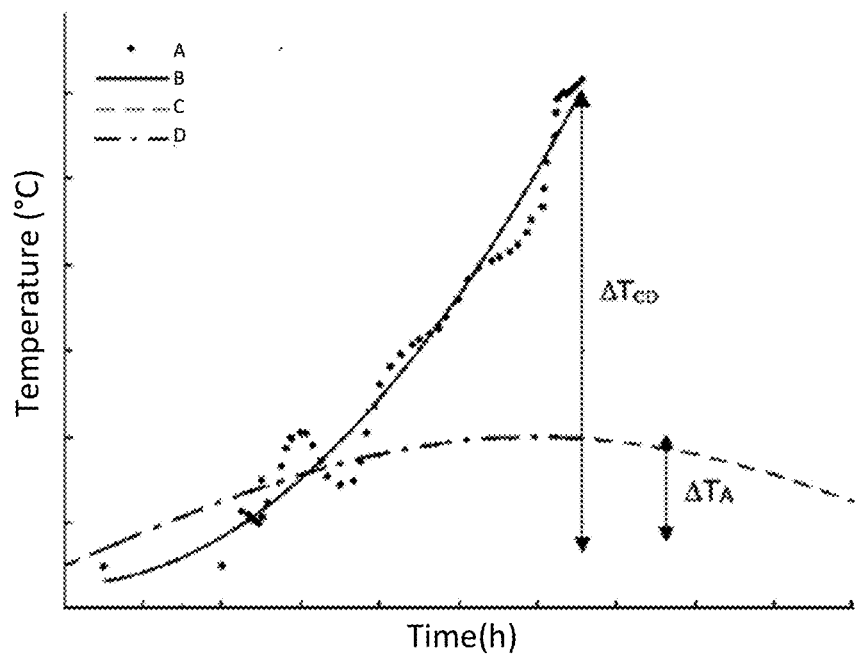
FIG. 8 shows a plot of temperature as a function of time of a portion having concrete.
Figure 9:
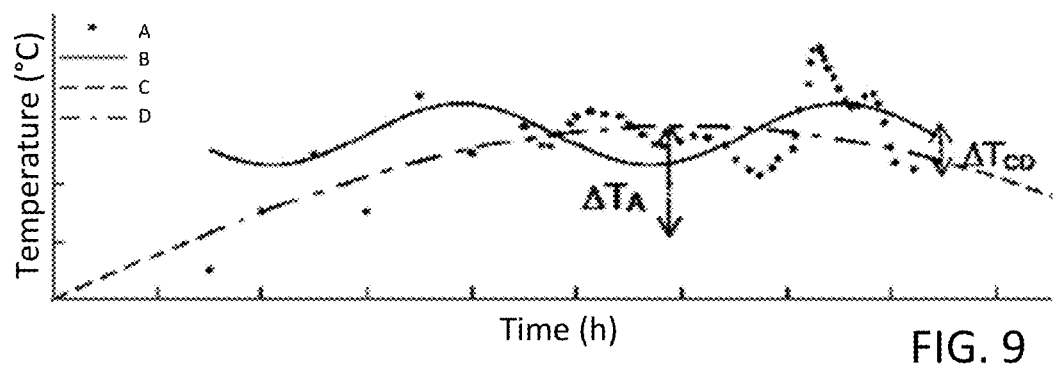
FIG. 9 shows a plot of temperature as a function of time of a portion not having concrete.

The value $\Delta T_A$ is the same in FIGS. 8 and 9, whereas the value $\Delta T_{CD}$ differs in said figures.

Example 3: Determination of Whether a Pixel Corresponds to Concrete

In the case of FIG. 8, it is seen that the value $\Delta T_{CD}$, corresponding to the indicating value, is greater than the value $\Delta T_A$, which has been used as threshold value in this example. Consequently, the pixel that originated the temperature profile of FIG. 8 will be identified as a pixel containing fresh concrete.

In contrast, in the case of FIG. 9, it is seen that the value $\Delta T_{CD}$ is lower than the value $\Delta T_A$. Consequently, the pixel that originated the temperature profile of FIG. 9 will be identified as a pixel not containing fresh concrete.

Example 4: Obtention of Binary Maps in Real Time

FIGS. 2 to 7 show graphic representations of different binary maps obtained by means of an embodiment of the method of the present invention, wherein the time ranges are 0.58 hours, 2.13 hours, 4.08 hours, 5.03 hours, 6.08 hours and 6.83 hours respectively. All the images share the same initial time.

Figure 2:
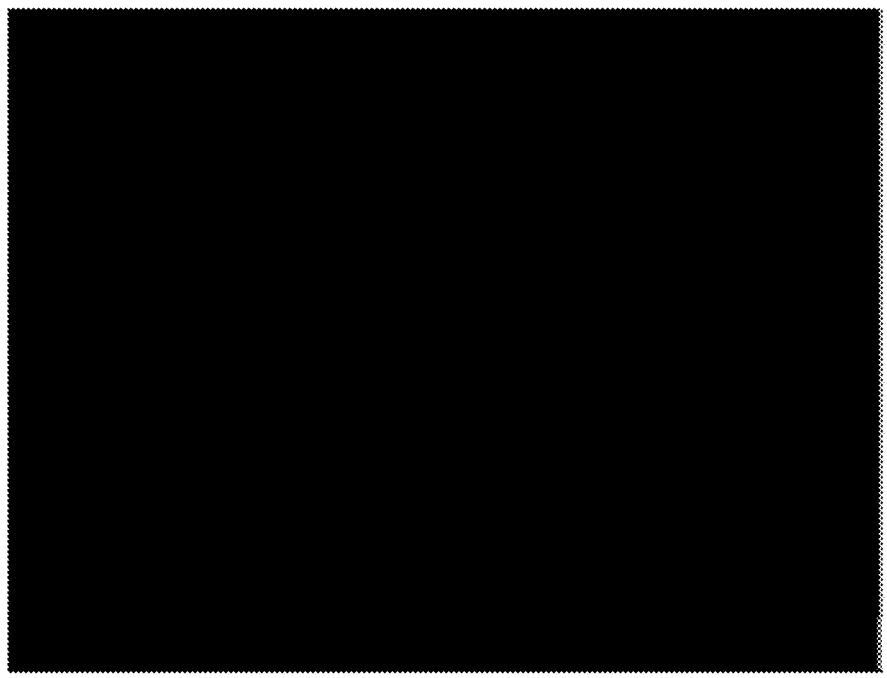
FIG. 2 shows a binary image of the region obtained by means of the method of the present invention in a time range of 0.58 hours.
Figure 3:
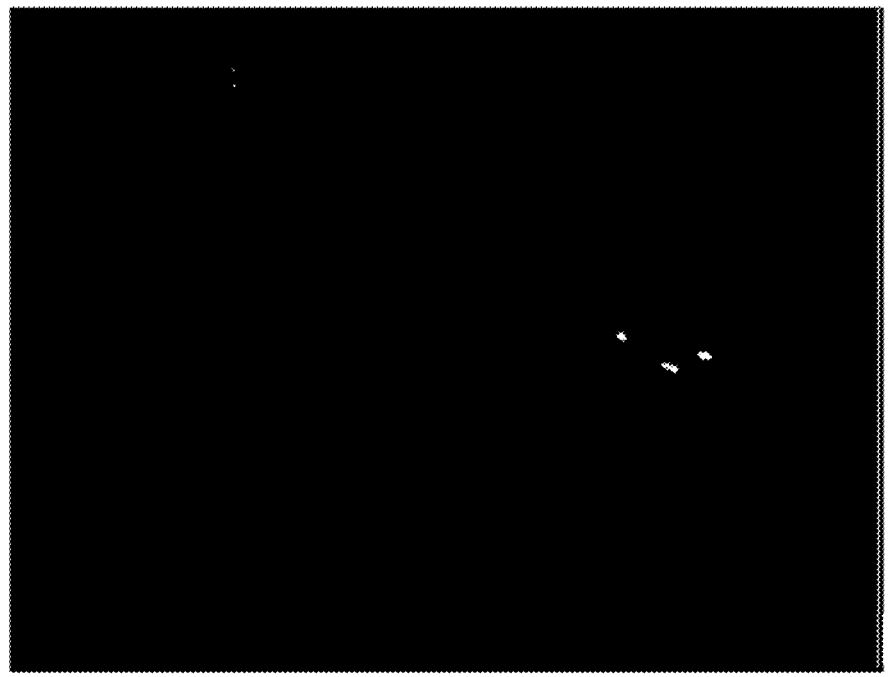
FIG. 3 shows a binary image of the region obtained by means of the method of the present invention in a time range of 2.13 hours.
Figure 4:
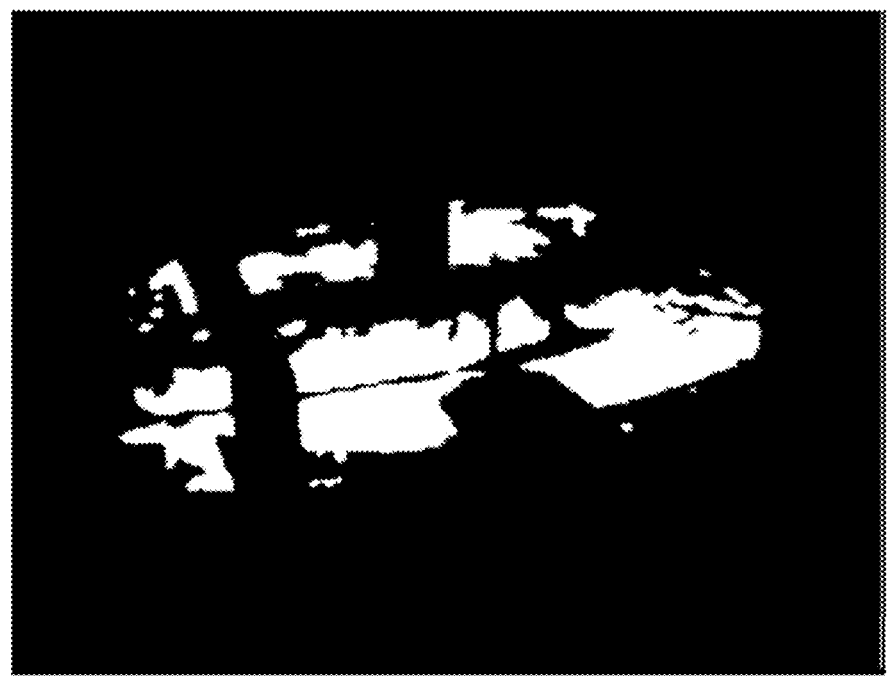
FIG. 4 shows a binary image of the region obtained by means of the method of the present invention in a time range of 4.08 hours.
Figure 5:
FIG. 5 shows a binary image of the region obtained by means of the method of the present invention in a time range of 5.03 hours.
Figure 6:
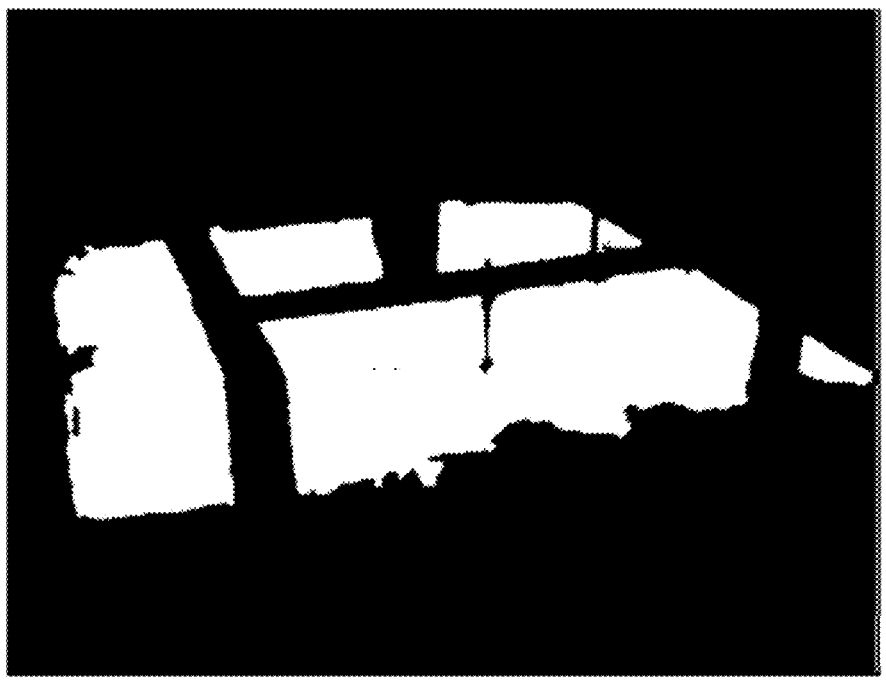
FIG. 6 shows a binary image of the region obtained by means of the method of the present invention in a time range of 6.08 hours.
Figure 7:
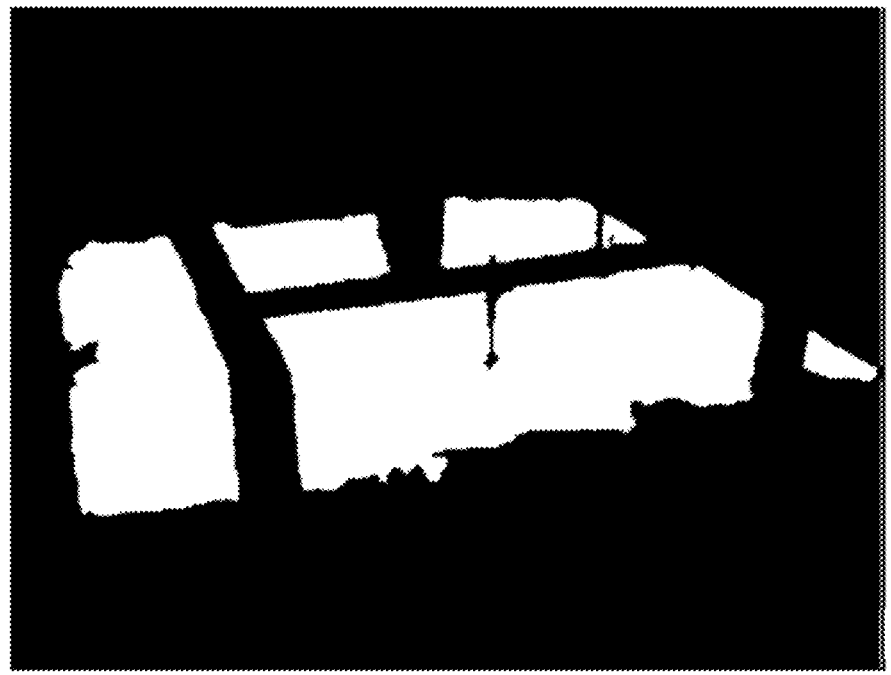
FIG. 7 shows a binary image of the region obtained by means of the method of the present invention in a time range of 6.83 hours.

It is seen that in the case of FIG. 2, no pixel has been identified as fresh concrete. In the case of FIG. 3, there exist some pixel being identified as fresh concrete, but most of the concrete sample has not been identified. In the case of FIG. 4, a great part of the sample has been correctly identified, but there exist portions, mainly in the boundaries, that have not been identified. Finally, in FIGS. 5, 6 and 7, a great part of the concrete sample has been satisfyingly detected.

The invention claimed is:

1. A system for detecting concrete in a region using infrared thermography, comprising:
   an infrared camera for obtaining a plurality of infrared thermography images in a time range from a region containing fresh concrete;
   an ambient temperature sensor for obtaining ambient temperature measurements;
   a processor connected to the camera and to the ambient temperature sensor that processes the plurality of infrared thermography images, analyzes pixels in the plurality of infrared thermography images for detecting concrete in the pixels, and processes the ambient temperature measurements; and
   a memory connected to the processor for storing the plurality of infrared thermography images and the ambient temperature measurements, wherein the processor further:
   obtains, for each pixel of the plurality of infrared thermography images obtained in the time range and stored in the memory, a temperature profile as a function of time;

adjusts each pixel's temperature profile as a function of time using a corresponding curve of temperature as a function of time, obtaining a plurality of curves of temperature as a function of time;

obtains an indicating value and a threshold value for each curve of temperature of each pixel, wherein the indicator value is selected from the group consisting of area under the curve of temperature as a function of time, difference of temperature between maximum and initial value of the curve of temperature as a function of time, ratio between maximum temperature and initial temperature of the curve of temperature as a function of time, average between maximum temperature and initial temperature of the curve of temperature as a function of time, and any weighing between the maximum temperature and the initial temperature of the curve of temperature as a function of time, and wherein the threshold value is obtained from the ambient temperature measurements; and compares the indicating value and the threshold value, wherein the processor defines that a pixel corresponds to concrete when the indicating value is greater than the threshold value.

2. The system for detecting concrete of claim 1, wherein the indicating value is the difference between the maximum temperature and the initial temperature in the time range and wherein the threshold value is a difference between a maximum ambient temperature measurement and a minimum ambient temperature measurement in the time range.

3. The system for detecting concrete of claim 1, the indicating value is the area under the curve in the time range and wherein the threshold value is selected from the group consisting of an area under the curve of ambient temperature measurements in the time range, and a product of an average ambient temperature measurement value in the time range and length of the time range.

4. A computer-implemented method for detecting concrete using infrared thermography, the computer-implemented method:

storing a plurality of infrared thermography images obtained from an infrared camera, and ambient temperature measurements obtained from an ambient temperature sensor, in a memory operatively connected to a processor which is operatively connected to the camera and the sensor, using the processor, wherein each image of the plurality of infrared thermography images corresponds to a region containing fresh concrete and wherein the plurality of infrared thermography images corresponds to a time range;

obtaining, with a processor, for each pixel of the plurality of infrared thermography images stored in the memory, a temperature profile as a function of time;

adjusting, with a processor, each pixel's temperature profile as a function of time using a corresponding curve of temperature as a function of time, obtaining a plurality of curves of temperature as a function of time;

obtaining, with a processor, an indicating value and a threshold value for each curve of temperature of each pixel, wherein the indicator value is selected from the group consisting of area under the curve of temperature as a function of time, difference of temperature between maximum and initial value of the curve of temperature as a function of time, ratio between maximum temperature and initial temperature of the curve of temperature as a function of time, average between maximum temperature and initial temperature of the curve of temperature as a function of time, and any weighing between the maximum temperature and the initial temperature of the curve of temperature as a function of time, and wherein the threshold value is obtained from ambient temperature measurements; and comparing, with a processor, the indicating value and the threshold value, wherein the processor defines that a pixel corresponds to concrete when the indicating value is greater than the threshold value.

5. The computer-implemented method of claim 4, wherein the curve of temperature, as a function of time, is selected from the group consisting of low coefficient Fourier series and low coefficient polynomials.

6. The computer-implemented method of claim 4, further comprises:

storing information corresponding to an ambient temperature profile in the memory;

obtaining a curve of the ambient temperature measurements as a function of time by using the processor; and obtaining the threshold value from the curve of the ambient temperature measurements as a function of time by using the processor.

7. The computer-implemented method of claim 4, wherein the indicating value is the difference between the maximum temperature and the initial temperature in the time range and wherein the threshold value is a difference between a maximum ambient temperature measurement and a minimum ambient temperature measurement in the time range.

8. The computer-implemented method of claim 4, wherein the indicating value is the area under the curve in the time range and wherein the threshold value is selected from the group consisting of an area under the curve of ambient temperature measurements in the time range, and a product of an average ambient temperature measurement value in the time range and length of the time range.

9. The computer-implemented method of claim 4, wherein the time range is between 3 hours and 12 hours.

10. The computer-implemented method of claim 4, wherein each image of the plurality of infrared thermography images is obtained with a periodicity between 5 minutes and 30 minutes.

11. The computer-implemented method of claim 4, wherein each image of the plurality of infrared thermography images is filtered before the obtention of the temperature profiles as a function of time.

12. The computer-implemented method of claim 11, wherein the plurality of infrared thermography images is filtered by using a gaussian filter.

13. The computer-implemented method of claim 4, further comprises generating an image of the region containing fresh concrete wherein the pixels identified as concrete are colored in a first color, the first color being contrasting to the image, the image being generated by using the processor.

14. The computer-implemented method of claim 4, further comprises generating a binary map of the region containing fresh concrete by using the processor.

* * * * *